United States Patent
Rosenkrans, Jr. et al.

[11] Patent Number: 5,952,222
[45] Date of Patent: Sep. 14, 1999

[54] FUNCTIONAL ENUCLEATION OF BOVINE OOCYTES

[75] Inventors: Charles F. Rosenkrans, Jr., Wheeler; Eddie J. Wagoner, Bradford, both of Ark.

[73] Assignee: The Board of Trustees of the University of Arkansas, Little Rock, Ark.

[21] Appl. No.: 08/691,850

[22] Filed: Aug. 2, 1996

Related U.S. Application Data

[60] Provisional application No. 60/002,252, Aug. 4, 1995.
[51] Int. Cl.$^6$ .................. C12N 5/06; C12N 5/00
[52] U.S. Cl. .......... 435/325; 435/375; 435/820; 800/2; 800/DIG. 6
[58] Field of Search .................. 435/346, 325, 435/6, 375, 820; 800/2, DIG. 6

[56] References Cited

U.S. PATENT DOCUMENTS 5,453,366   9/1995   Sims et al. .................. 435/172.3

*Primary Examiner*—David Saunders
*Assistant Examiner*—F. Pierre Vander Vegt
*Attorney, Agent, or Firm*—J. M. (Mark) Gilbreth; Robert W. Strozier; Gilbreth & Strozier, P.C.

[57] ABSTRACT

A method of preparing a recipient oocyte from a target zona-intact or zona-free oocyte by centrifuging the oocyte against a density gradient material to force the chromosomal material to pass through the cytoplasmic membrane.

3 Claims, 1 Drawing Sheet

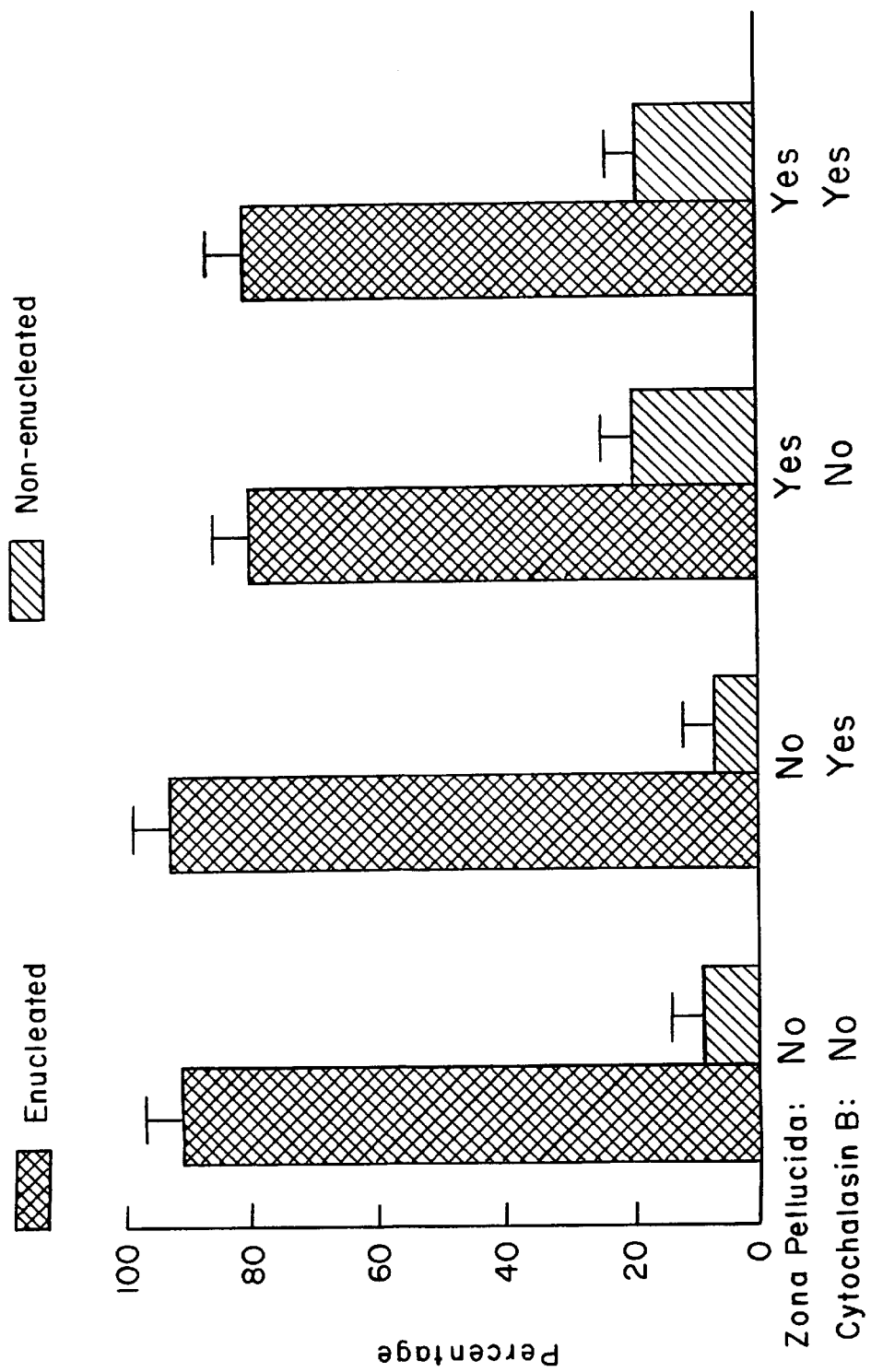

5,952,222

FUNCTIONAL ENUCLEATION OF BOVINE OOCYTES

RELATED APPLICATION DATA

This application claims priority from U.S. Provisional Application Ser. No. 60/002,252, filed Aug. 4, 1995.

BACKGROUND OF THE INVENTION

1. Field of the Invention

The present invention relates to methods of processing oocytes to obtain recipient oocytes for cloning, and to methods of cloning.

2. Description of the Related Art

The livestock industry in the United States is a $484 billion industry, with 99 million head of cattle producing 19 billion pounds of beef and 10 million dairy cows producing 136 billion pounds of fluid mild (USDA, 1990). Techiques exist to allow a producer to select and mate superior bulls and cows for specific traits in superior offspring. Once such a superior offspring is obtained, it is desired to produce identical animals or "clones".

Early cloning techniques included surgical bisection of an early stage embryo, prior to it losing totipotency, into halves or quarters. While these early surgical bisection techniques did increase the number of identical animals produced, these techniques were limited to 2 to 4 identicals.

Later cloning developments have allowed more advanced embryos (8–32 cells) to be manipulated into retaining totipotency of each blastomere through nuclear transplantation to oocytes, thus increasing the number of identicals up to the range of 8 to 32 identicals.

With current state of the art, mammalian offspring can be produced by nuclear transfer, which offers the potential of a much larger or (theoretically) an unlimited number of identicals. The proportion of manipulated nuclear transplant embryos developing to offspring is approximately 1% in pigs (Prather R. S., M. M. Simms, and N. L. First. 1989. Nuclear transplantation in early pig embryos. Biol. Reprod. 41:414, herein incorporated by reference), 1% (Prather R. S., F. L. Barnes, M. M. Simms, J. M. Rob, W. H. Eyestone, and First N. L. 1987. Nuclear transplantation in the bovine embryo: assessment of donor nuclei and recipient oocyte. Biol. Reprod. 37:859, herein incorporated by reference) and 4% (Bondioli, K. R., M. E. Westhusin and C. R. Loony. 1990. Production of identical bovine offspring by nuclear transfer. Theriogenology 33:165, herein incorporated by reference) in cattle, approximately 4% in sheep (Smith L. C. and I. Wilmut. 1989. Influence of nuclear and cytoplasmic activity on the development in vivo of sheep embryos after nuclear transplantation. Biol. Reprod. 40:1027, herein incorporated by reference) and 4% in rabbits (Stice S. L., and J. M. Robl. 1988. Nuclear reprogramming in nuclear transplant rabbit embryos. Biol. Reprod. 39:657, herein incorporated by reference). A portion of the decreased developmental potential of nuclear transferred oocytes may have been due to polyploidy, as indicated by the reported enucleation rates. The enucleation rates varied from 60% in cattle (Prather et al., 1987) to 92% in rabbits (Stice and Robl, 1988). Sheep (Smith and Wilmut, 1989) and pigs (Prather et al., 1989) had rates of 68% and 74%, respectively.

While these nuclear transfer techniques for cloning identical embryos exist, they are rather costly and inefficient. With such techniques, oocytes are harvested from donor animals, with the metaphase plate subsequently removed to produce recipient oocytes. This requires a skilled technician who must remove the metaphase plate utilizing micromanipulators, and then deposit the donor blastomere through the zona pellucide into the recipient oocyte perivitelline cavity. After blastomere insertion the blastomere and recipient are fused, for example, with electrical current, chemical agent(s) or viral agent(s), and placed into development.

Removing the metaphase plate using micromanipulators is extremely time consuming, with a skilled technician capable of removing from about 100 to 200 in a 4 to 6 hour period.

Thus, there is a need in the art for an improved method of preparing recipient oocytes.

There is another need in the art for a method of preparing recipient oocytes which is less time consuming than the current methods.

There is still another need in the art for an improved method of cloning.

These and other needs in the art will become apparent to those of skill in the art upon review of this specification, including its drawings and claims.

SUMMARY OF THE INVENTION

It is one object of the present invention to provide for an improved method of preparing recipient oocytes.

It is another object of the present invention to provide for a method of preparing recipient oocytes which is less time consuming than the current methods.

It is still another object of the present invention to provide for an improved method of cloning.

These and other objects of the present invention will become apparent to those of skill in the art upon review of this specification, including its drawings and claims.

According to one embodiment of the present invention there is provided a method of forming recipient oocytes. The method generally includes taking cumulus-free, and optionally zona-free oocytes, and separating the chomosomal material from the oocyte by centrifuging against a density gradient material.

According to another embodiment of the present invention, there is provided a method of cloning. The method generally includes fusing a recipient oocyte as described above, with a donor cell.

BRIEF DESCRIPTION OF THE DRAWINGS

FIG. 1 shows the data from Example 4, in which Oocytes were functionally enucleated using four different approaches. All oocytes were centrifuged on a percoll density gradient at 12,000×g for 5 min. Prior to centrifugation oocytes had their zona pellucida removed or they remained intact and/or were incubated with cytochalasin B (7.5 $\mu$g/ml) for 1 h prior to centrifugation. Oocytes were considered enucleated if chromosomal material was either outside the cytoplasmic membrane, not found, or fragmented. Absence of zona pellucida increased (P<0.05) the percent of oocytes that were enucleated; however, pretreating oocytes with cytochalasin B did not alter (P>0.1) enucleation rates.

DETAILED DESCRIPTION OF THE INVENTION

Oocytes utilized in the practice of the present invention are generally obtained from donor animals by methods which are well known to those of skill in the art. Such methods include surgical removal of oocytes from the ovaries of cows. It should be understood that the present invention is not to be limited to any particular method of harvesting oocytes, but that any suitable method may be utilized.

Once harvested, these oocytes with cumulus cells attached, (cumulus oocyte complexes) are subsequently rinsed with, and then stored in a preparation medium. Preparation medium are well known to those of skill in the art, and the present invention is not intended to be limited to any particular preparation medium. Any suitable preparation medium may be utilized in the present invention. Such preparation medium are generally buffered salt solutions.

In the practice of the present invention, the harvested oocytes must subsequently be matured into a fertilizable oocyte, which generally requires maturation for a limited time, in a maturation medium at a controlled temperature and atmosphere. As, these maturation conditions will tend to vary for each animal species, the present invention is not to be limited to any set of conditions, but rather should accommadate a broad range of animal oocytes. For example, in a maturation medium at 39° C., in a 5% $CO_2$/95% air atmosphere, maturaturation can occur in about 24 to 30 hours for bovine and ovine, and in about 36 to 42 hours for porcine.

After maturation, it is generally necessary to strip the cumulus cells from the cumulus oocyte complex in order to facilitate subsequent processing. Methods of stripping such cumulus cells from oocytes are well known and any suitable method may be utilized. For example, the cumulus cells may be mechanically stripped from the oocyte.

In the practice of the present invention, the zona pellucida may optionally be removed from the oocyte. Methods of removing the zona pellucida from an oocyte are well known, and any suitable method may be utilized in the present invention. Non-limiting examples of methods include contacting with protease and/or an acidified salt solution.

The oocytes, whether zona-intact or zona-free, are subsequently centrifuged to separate the metaphase plate from the oocyte. This centrifugation is generally accomplished utilizing a density gradient material, such as PERCOLL available from Sigma company of St. Louis.

In this centrifugation, the density of the density gradient material must be greater than the density of the oocyte. The oocyte is centrifuged against the oocyte at a centrifugal force that is at least great enough to force the chromosomes through the cytoplasmic membrane, but not so great as to destroy the cytoplasmic membrane. Additionally, the porosity or hardness of the density gradient material must be sufficiently low so that the chromosomes will pass through the cytoplasmic membrane, but not so low as to allow the cytoplasmic membrane to pass through the density gradient material. In the examples of the present invention, a 90% PERCOLL was utilized, although it is believed that PERCOL as low as about 30% could be utilized.

Multiple layers of the density gradient material may be utilized, provided that there is at least one layer which meets the above description.

In the case of centrifuging a zona-intact oocyte, the chromosomes will tend to accumulate in the perivitelline space between the cytoplasmic membrane and the zona. In the case of centrifuging a zona-free oocyte, the chromosomes will either accumulate between the cytoplasmic membrane and the density gradient material, or pass through the density gradient material, depending upon the porosity of the density gradient material. If the porosity is sufficiently high, the chromosomes will tend to pass through the material.

It must also be appreciated, that the centrifugal force required will also be a function of the centrifuging time. Shorter times will tend to require a greater centrifugal force than longer times. It must also be appreciated, that the centrifugal force required will also vary with each oocyte species. Finally, it must be further appreciated, that certain agents, my affect the cytoplasmic membrane, such that less centrifugal force is necessary to force the chromosomes through the cytoplasmic membrane. As non-limiting examples, cytochalasin B or D will affect such a change.

Generally, the centrifugal force utilized in the present invention is at least about 5000×g. Preferably, the centrifugal force utilized in the present invention is greater than about 9500×g. More preferably, the centrifugal force utilized in the present invention is at least about 10,000×g, and even more preferably at least about 12000×g. Generally, the upper limit for the centrifugal force utilized will be on the order of about 150,000×g and higher. Preferably, the upper limit for the centrifugal force utilized in the present invention is about 100,000×g. More preferably, the upper limit for the centrifugal force utilized in the present invention is about 65,000×g, and more, and even more preferably at least about 50,000×g.

Centrifuging times must be sufficient to allow the chromosomes to pass through the cytoplasmic membrane at the centrifugal force utilized, and yet prevent destruction of the oocyte. Generally, the centrifuging time will range from a few seconds to hours. Preferably, the centrifuging time will range from about 3 minutes to about 3 hours, and more preferably will range from about 5 minutes to about 1 hour.

The recipient oocytes of the present invention, both zona-intact, and zona-free, will find utility in the preparation of cloned embryos.

Once the chromosomes are separated the recipient oocyte is recovered and subsequently contacted with a donor cell. The donor cell and the recipient oocyte are fused together utilizing chemical, electrical or viral techniques as are known in the art, to form cloned embyos. The cloned embryos of the present invention will find utility in producing cloned animals.

EXAMPLES

The present invention will now be further explained by the following Examples 1–4 which are not intended to limit the present invention in any manner.

Examples 1 and 2

Oocyte recovery, maturation, fertilization and developement, for Examples 1 and 2, are as follows.

Oocyte Recovery and Maturation

Ovaries (suspended in saline [0.9% NaCl; 30±2° C.] in insulated containers) were transported from a slaughterhouse to the laboratory. Upon arrival, ovaries were rinsed with fresh saline and placed back into the insulated container. Visible follicles were sliced with a razor blade and rinsed with Delbecco's phosphate buffered saline (DPBS). Follicular contents and rinse medium were allowed to settle in sterile beakers and the liquid decanted. Cumulus-oocyte complexes (COC) were gathered and rinsed in DPBS (3 times) and maturation medium (1 time) prior to being placed in the maturation medium. Maturation of COC (100/well) was for 22±2 h in four-well plates with each well containing 0.5 ml of maturation medium (Medium 199+estrous cow serum (20%)+HEPES (10 mM)+antibiotic/antimycotic (1%)) in a humidified incubator (39° C.) with an atmosphere of 5% $CO_2$ in air.

Oocyte Fertilization and Development

After maturation, cumulus cells were manually stripped from COC. Oocytes were rinsed three times through CR1aa (8) before being placed into fertilization plates. Four-well plates were used for fertilization, each well contained 0.5 ml of CR1aa+heparin (2 µg/ml)+PHE stock (20 µl/0.5 ml; final concentrations were penicillamine [18.2 µM], hypotaurine [9.1 µM], and epinephrine [1.8 µM]; see 9)+motile sperm ($5 \times 10^5$) and approximately 100 oocytes. At 42±3 h post-insemination, cleavage rate was assessed.

Analyses

Examples 1 and 2 were analyzed with the general linear model procedure with replicate and treatment effects in the model (SAS. SAS User's Guide: Statistics. Cary N.C., Statistical Analysis System Institute Inc, 1985). Prior to analysis, percentage data were transformed using the arcsine square root function. If the main effects F-test was significant, the means were separated using the PDIF function of SAS. Means are presented as the least square means and their appropriate standard error.

Example 1

This example was designed to determine the effects of centrifugation on metaphase II oocytes. Oocytes were matured in vitro, cumulus cells removed, and one-half of the oocytes on each day were randomly selected for centrifugation. Those oocytes (approximately 50/tube) that were selected for centrifugation were placed into microcentrifuge tubes containing CR1aa with HEPES (10 mM) and then centrifuged at 12,000×g for 4 min prior to fertilization. Oocytes not selected for centrifugation were treated in a similar manner without centrifugation.

Results

Eight replicates utilizing 1571 oocytes (centrifuged n=1091 vs. non-centrifuged n=480) were used to determine the effects of centrifugation on oocyte cleavage. Centrifugation of metaphase II oocytes prior to fertilization decreased (P<0.05) cleavage rate (79.5 vs. 70.4%, respectively for control and centrifuged) During the first three replicates it was noted that following centrifugation ooplasm took on one of two forms, stratified or granulated. Therefore, during the last five replicates oocytes were sorted based on ooplasm form, and cleavage rate assessed for each ooplasm type. Oocytes with stratified ooplasm had clearly defined gradients in the ooplasm; however, the granulated type of ooplasm had dark spherical clumps in the ooplasm. As presented in Table 1, there was no significant difference in the cleavage rate of the oocytes with the two different ooplasm types.

TABLE 1

Effect of ooplasm type on bovine oocyte cleavage rate (Example 1).

| Ooplasm type | No. Oocytes | Cleaved, % |
| --- | --- | --- |
| Non-centrifuged | 201 | 75.6[a] |
| Stratified | 264 | 64.0[b] |
| Granulated | 387 | 64.3[b] |
| SEM | | 2.5 |

[a,b]Percentages with different superscripts differ (P < 0.05).

Example 2

Interactive effects of centrifugation, and ultraviolet (UV) light on the cleavage rate of bovine oocytes and fate of the nuclear material were determined in this example. Oocytes were randomly allotted to treatment in a complete-block designed experiment with treatments arranged as a 2×2 factorial. Main effects were centrifugation (as in Example 1) and UV light (0 or 254 nm delivered at 8 mw/cm² for 2 min.). After maturation, oocytes were treated, fertilized and at 42±3 h post-fertilization cleavage rates were assessed and those oocytes not cleaving were stained with Hoechst 33342. Oocyte DNA was located using an inverted microscope equipped with epifluorescence.

Results

Nine replicates utilizing 1749 oocytes were used to determine the effects of centrifugation and UV light on oocyte cleavage rate and the fate of nuclear material following treatment. Percentage of oocytes cleaving after centrifugation was decreased (P<0.07; 34.1 vs. 26.5%, respectively for control and centrifuged). Exposing oocytes to UV light also decreased cleavage rate (P<0.07; 35.4 vs. 25.2%, respectively for control and UV exposed). There were no (P>0.1) interactive effects of centrifugation and UV light on cleavage rates of oocytes. However, treating metaphase II oocytes with both centrifugation and UV light prior to fertilization resulted in a smaller (P<0.01) percentage of the non-cleaved oocytes having their DNA inside the cytoplasmic membrane (Table 2). Both of the main effects (centrifugation and UV light exposure) also decreased (P<0.05) the percentage of oocytes with nuclear material within the cytoplasmic membrane.

TABLE 2

Effects of centrifugation and ultraviolet light on oocyte cleavage percentage and nuclear placement of non-cleaved oocytes (Example 2).

| | Treatments[a] | | | | |
| --- | --- | --- | --- | --- | --- |
| Item | CON | UV | CENT | UV*CENT | SEM |
| No. oocytes | 451 | 425 | 445 | 428 | |
| Cleaved[b], % | 38.9 | 29.2 | 31.9 | 21.1 | 4.8 |
| Chromosomes Inside, % | 82.6[c] | 84.5[c] | 86.9[c] | 50.8[d] | 5.1 |

[a]Treatments were CON = control, UV = ultraviolet light exposure, CENT = centrifugation, and UV*CENT = both UV light exposure and centrifugation.
[b]Interactive effects of UV*CENT did not affect (P > 0.1) the percentage of oocytes that cleaved; however, UV and CENT independently decreased cleavage rates (see text).
[c,d]percentages within the same row with different superscripts differ (P < 0.01).

Discussion of Results of Examples 1 and 2

Results from Example 1 indicate that centrifugation of metaphase II oocytes prior to fertilization decreases their developmental potential. Wall and Hawk found that centrifugation of pronuclear oocytes decreased the developmental rate of bovine oocytes cultured in the rabbit oviduct (Wall R. J., Hawk H. W. Development of centrifuged cow zygotes cultured in rabbit oviducts. J Reprod Fert 1988; 82:673–680). Collectively, these results indicate that bovine oocytes at the metaphase II and pronuclear stages are developmentally impaired by centrifugation.

Ooplasm that is stratified after centrifugation has been noted in oocytes from cattle (Robl. J. M., Prather R., Barnes F, Northey D, Gilligan B, First N. L. Nuclear transplantation in bovine embryos. J Anim Sci 1987; 64:642–647, herein incorporated by reference), hamsters (Yang C H, Yanagimachi R, Yanagimachi H. Morphology and fertilizability of zona-free hamster eggs separated into halves and quarters by centrifugation. Biol Reprod 1989; 41:741–752, herein incorporated by reference), mice (Gresson RAR. Effect of ultracentrifuging the oocytes of the mouse. Nature 1938; 142:957–958, herein incorporated by reference), and humans (Aykroyd OE. The effects of ultracentrifuging human oocytes. Proc Royal Irish Acad Dublin Sec. B 1941; 46:101–111, herein incorporated by reference); however, there was no previous mention of the granulated type of ooplasm. Directly comparing the developmental competence of the two types of ooplasm indicated no difference. This suggests that there may be structural differences of the cytoplasmic skeleton because the alternative, degradation of the oocyte, would result in less viability. Although, we would point out that cleavage rate is not as good of an indicator of viability as is development to a transferable stage (i.e., morula or blastocyst).

Oocytes from rabbits (Yang X, Zhang L, Kovacs A, Tobback C, Foote R H. Potential of hypertonic medium treatment for embryo micromanipulation; II assessment of nuclear transplantation methodology, isolation, subzona insertion, and electrofusion of blastomeres to intact or functionally enucleated oocytes in rabbits. Mol Reprod Dev 1990; 27:118–129, herein incorporated by reference) and mice (Tsunoda Y, Shioda Y, Onodera M, Nakamura K, Uchida T. Differential sensitivity of mouse pronuclei and zygote cytoplasm to Hoechst staining and ultraviolet irradiation. J Reprod Fert 1988; 82:173–178, herein incorporated by reference) have been functionally enucleated using Hoechst 33342 and UV light. Tsunoda enucleated murine oocytes at the metaphase II stage by exposing them to 15 seconds of UV irradiation after Hoechst 33342 staining. X. Yang found that Hoechst 33342 stained rabbit oocytes required a 3-minute exposure to UV light to become functionally enucleated. A combination of centrifugation and cytochalasin D were used to achieve functional enucleation in zona-free hamster oocytes (Yang C H, Yanagimachi R, Yanagimachi H. Morphology and fertilizability of zona-free hamster eggs separated into halves and quarters by centrifugation. Biol Reprod 1989; 41:741–752, herein incorporated by reference). When hamster oocytes without zona pellucida were treated with cytochalasin D and centrifuged for 30 seconds, the chromosomes were located at the centripetal pole. Increasing the centrifugation time to 1 minute or greater resulted in ooplasm free of chromosomes. In the present study, the zona pellucida was not removed nor was the cytoskeleton treated with skeletal relaxing agents; however, centrifugation and UV light exposure resulted in a greater percentage of the chromosomes in the perivitelline space (i.e., functionally enucleated). The low cleavage rates in Exp. 2 may have been caused by a phenomenon noted by Lawitts and Biggers (Lawitts J A, Biggers J D. Overcoming the 2-cell block by modifying standard components in a mouse embryo culture medium. Biol Reprod 1991; 45:245–251, herein incorporated by reference). They found that moving oocytes through different media with numerous handling procedures was detrimental to embryo development. Another possibility is that fertilization rate was altered by the various treatments; however, oocyte fertiliztion rate was not determined. The mechanism by which centrifugation and ultraviolet light interact resulting in increased enucleation rates of metaphase II oocytes is unknown. However, we speculate that the ultraviolet light may increase the rigidity of chromosomal DNA resulting in a genome that is more easily forced into the vitelline space via centrifugation.

Collectively, these data indicate that bovine oocytes can be functionally enucleated. Manually removing the nuclear material from bovine oocytes is a laborious process that requires technical expertise for successful enucleation rates. Therefore, functional enucleation offers many advantages to manual enucleation. Once the technique is refined, functional enucleation could be routinely used for nuclear transfer, resulting in a simpler and more efficient technique.

Examples 3 and 4

Oocyte recovery and maturation for Examples 3 and 4 are as follows.

Oocyte Recovery

Ovaries were collected from beef and dairy cows slaughtered at an abbatoir and transported in normal saline (0.9% NaCl) at 32–34° C. After arrival the ovaries were rinsed, counted, and placed into fresh normal saline (36° C.). Follicles (2–5 mm) were aspirated with a 12-ml syringe equipped with an 18-gauge needle. The aspirated follicular fluid and tissue were centrifuged (5 min; 500×g) to form a concentrated pellet. The pellet was resuspended in recovery medium (DPBS with 2% estrous cow serum (ECS) and 1% antibiotic-antimycotic (ABAM)). Following dilution, cumulus-oocyte complexes (COC) were located using a stereomicroscope. The COC were rinsed three times in recovery medium and once in maturation medium (M-199 with ECS (20%), ABAM (1%) and Hepes (10 mM)) before being placed into the maturation plate.

Oocyte Maturation

The maturation plates consisted of four-well plates with each well containing 500 $\mu$l of maturation medium. The COC were placed into a humidified incubator (39° C.; 5% $CO_2$ in air) and allowed to mature for 24±2 h. When maturation was completed the oocytes were mechanically stripped of cumulus cells by repeated pipetting and were placed into recovery medium to await treatment.

Statistical Analysis

Data of Examples 3 and 4 were analyzed using the General Linear Model procedure and least-squares means option of SAS (1990). All treatments were conducted on each day, which represented replicate effects; therefore, each model contained replicate and main effects for each experiment. Prior to analysis, percentage data (inside, outside, and not found) were transformed using the arsine square-root function. However, percentages are presented in the tables and figure as the least-squares means with their appropriate pooled standard error.

Example 3

Oocytes were randomly assigned to a 2×2 factorial treatment structure. Main effects were cytochalasin B (0 or 7.5 $\mu$g/ml) and centrifugation (12,000×g) for 2 or 3 min. This experiment was conducted to determine the effects of cytochalasin B treatment prior to centrifugation on chromosome placement of zona-free bovine oocytes.

The zona pellucidae were removed from the oocytes using protease (1%) in DPBS. One half of the zona-free oocytes were placed in CR1aa (Rosenkrans and First, 1994, Effect of free amino acids and vitamins on cleavage and developmental rate of bovine zygotes in vitro. J. Anim. Sci. 72:434, herein incorporated by reference), and the other half were placed in CR1aa with cytochalasin B (7.5 $\mu$g/ml) for 1 h (39° C.;5% $CO_2$). One-half of each cytochalasin group was centrifuged for 2 min and the other half for 3 min. Following treatment, the location of metaphase II chromosomes for each oocyte was determined using Hoechst 33342 (1 $\mu$g/ml) staining and visual appraisal with an inverted microscope equipped with epiflourescence. Metaphase II chromosome placement was classified as inside the cytoplasmic membrane, outside but still adjacent to the cytoplasmic membrane, or not found. Oocytes were classified as not found if there was no Hoechst 33342 stained nuclear material in or adjacent to the oocyte, or if the oocyte had fragmented DNA.

Results

One hundred eighty-three oocytes from four replicate days were utilized in this Example. Treatment with cytochalasin B had no significant effect on the percentage of chromosomes found inside, outside or not found (Table 3). Furthermore, centrifugation time (2 or 3 min) had no significant effect on chromosome placement (Table 3). However, we observed a larger number of oocytes degraded into cytoplasmic droplets when centrifuged for 3 min than when centrifuged for 2 min.

TABLE 3

Effects of centrifugation time and
cytochalasin B on chromosome placement of bovine oocytes

| | Cytochalsin B | | | | |
|---|---|---|---|---|---|
| | 0 μ/ml Centrifugation, min | | 7.5 μ/ml Centrifugation, min | | |
| Item | Two | Three | Two | Three | SEM |
| No. of oocytes | 44 | 49 | 39 | 51 | |
| Chromosome placement[a] | | | | | |
| Inside, % | 152.3 | 57.5 | 58.7 | 48.3 | 5.89 |
| Outside, % | 6.8 | 8.9 | 5.1 | 11.4 | 4.77 |
| Not Found, % | 40.9 | 33.6 | 36.2 | 40.3 | 8.49 |

[a]After centrifugation at 12,000 × g in CR1aa all oocytes were stained with Hoechst 33342, and metaphase II chromosomes were located using an inverted microscope equipped with epiflourescence. Classifications were inside the cytoplasmic membrane, outside but still adjacent to the cytoplasmic membrane, and not found, in which there was no stained nuclear material or only fragmented DNA. Percentages were not affected (P > .1) by either centrifugation time or treatment with cytochalasin B for 1 h prior to centrifugation.

Even though experiment 1 showed no significant differences among treatments, the level of enucleation is significant. The published results for manual enucleation of bovine oocytes show an efficiency of 50 to 60% (Prather R. S., F. L. Barnes, M. M. Simms, J. M. Rob, W. H. Eyestone, and First N. L. 1987. Nuclear transplantation in the bovine embryo: assessment of donor nuclei and recipient oocyte. Biol. Reprod. 37:859; Robl J. M., and S. L. Stice. 1989. Prospects for the commercial cloning of animals by nuclear transplantation. Theriogenology 31:75, all herein incorporated by reference). Recently, methods of manual enucleation have included the use of Hoechst 33342 stain during enucleation and have presumably achieved 100% enucleation rates (Collas P., and F. L. Barnes. 1994. Nuclear transplantation by microinjection of inner cell mass and granulosa cell nuclei. Mol. Reprod. Dev. 38:264, 1994; Stice S. L., C. L. Keefer, and L. Matthews. 1994. Bovine nuclear transfer embryos: Oocyte activation prior to blastomere fusion. Mol. Reprod. Dev. 38:61, all herein incorporated by reference). The percent "not found" plus "outside," which is equivalent to total enucleation, ranges from 41 to 51% for bovine oocytes centrifuged without zona pellucidae and without a density gradient. Therefore, centrifugation can result in enucleation rates similar to those published for manual enucleation when staining was not included in the procedure.

Example 4

Treatments were arranged as a 2×2 factorial with main effects of zona pellucida (with or without) and cytochalasin B (0 or 7.5 μg/ml). These treatments were designed to determine the effects of cytochalasin B treatment on zona-intact and zona-free bovine oocytes centrifuged on a percoll gradient.

Oocytes were randomly assigned to either zona-intact or zona-free groups. Zona pellucidae were removed as in Example 3. Each of the zona groups were split and treated with or without cytochalasin B as described in Example 3. After cytochalasin B treatment, the four groups of oocytes were placed on density gradients formed in microcentrifuge tubes. Density gradients consisted of two layers: the top layer was CR1aa (500 μl) and the bottom layer consisted of 90% percoll (500 μl) (Rosenkrans C. F. Jr., G. Q. Zeng, G. T. McNamara, P. K. Schoff, and N. L. First. 1993. Development of bovine embryos in vitro as affected by energy substrates. Biol. Reprod. 49:459, herein incorporated by reference). The oocytes and percoll gradients were centrifuged for 5 min at 12000×g. After centrifugation, each layer was pipetted into different wells of a 24-well plate and each well received Hoechst 33342 (1 μg/ml) stain. Metaphase II chromosome placement was determined as in Example 3 above.

Results

Three replications with a total of 170 oocytes were used in this Example. Treatment with cytochalasin B had no significant effect on the chromosome placement. Furthermore, there was no interactive effect between cytochalasin B and the presence or absence of a zona pellucida (FIG. 1) on chromosome location after treatment. In contrast, zona pellucida treatment alone had an effect (P<0.05) on all three of the criteria evaluated (Table 4). The percentage of oocytes with no visible chromatin (not found) was higher (P<0.02) in zona-free (86%) than in zona-intact (60%). The zona pellucida had the opposite effect on the outside percentages (zona-intact 21% and zona-free 6%). As in Example 3, a few of the zona-free oocytes without cytochalasin B treatment were small cytoplasmic droplets after centrifugation.

TABLE 2

Effects of zona pellucida on chromosome
placement of bovine oocytes centrifuged on a density gradient

| | Zona pellucida | | |
|---|---|---|---|
| Item | Intact | Removed | SEM |
| No. of oocytes | 88 | 82 | |
| Chromosome placement[a] | | | |
| Inside, % | 19.0 | 7.6 | 3.55[b] |
| Outside, % | 20.6 | 6.4 | 3.79[b] |
| Not Found, % | 60.4 | 86.0 | 4.97[b] |

[a]See Table 3 for metaphase II classifications.
[b]Precentages were different (P < .05).

Example 4 indicated that the removal of the zona pellucida increased the functionally enucleated ("not found" plus "outside") percent by approximately 11%. An enucleation rate of near 90% is a definite improvement over the 50 to 60% published for bovine oocytes (Prather et al, 1987; Robl and Stice, 1989). Such enucleation rates are comparable to the ≧90% recorded for rabbit oocytes (Stice and Robl, 1988) and manual enucleation of bovine oocytes coupled with staining. The improved enucleation efficiency of the present invention was accomplished using a percoll gradient. Yang et al. (1989) utilized a three-layer percoll gradient. In their study, zona-free hamster oocytes were loaded on a tri-layer percoll (7.5/30/45%) gradient. During centrifugation (9500×g) the oocytes came to rest in the 30% layer. The oocytes remained in this layer throughout centrifugation and even separated into light and heavy halves while suspended in this layer. Percoll gradients also have been used to enucleate hybrid cell lines (Yukui and Ponce De Leon, 1992). The cells were placed on a 1:1 (vol/vol) gradient of percoll and RDG medium containing cytochalasin B (20 µg/ml). That gradient produced 2 layers, microcells, and karyoplasts and some whole cells.

Percoll gradients have been shown to be an efficient way to functionally enucleate hamster oocytes and hybrid cell lines. Furthermore, our data indicate that percoll gradients enhance functional enucleation of bovine oocytes. The >80% enucleation rate in Example 4 for bovine oocytes is comparable to or better than the accepted industry standard. Previous research has indicated that bovine oocytes can be matured without an intact zona pellucidae and develop to viable offspring (Xu et al., 1991).

Yang et al. (1989) found that 100% of the DNA material in cytochalasin-D-treated zona-free hamster eggs disappeared after 60 to 90 sec of centrifugation (9500×g). The results of the above experiments do not show an advantage to cytochalasin B treatment of zona-free bovine oocytes prior to centrifugation. Without being limited by theory, this could be attributed to a difference in the structure of the oocytes or a difference in the actions or potency of cytochalasin D compared to cytochalasin B. Cytochalasin D and B are both bacteria derivatives belonging to a family of about 10 isolated cytochalasins. Both cytochalasin D and B act as cytoskeleton antagonists by disrupting the function of microfilaments by inhibiting actin formation. Yang et al. (1989) treated hamster oocytes for 30 min with 10 µM cytochalasin D; however, in the examples above bovine oocytes are treated with 7.5 µg/ml cytochalasin B for 1 h. Treating oocytes with cytochalasin B (7.5 µg/ml) has been successfully used with mice (Prather and First, 1986), rabbits (Collas and Robl, 1990), and cattle (Nagai, 1992).

While the present invention has been illustrated mainly by reference to bovine oocytes, the present invention is not to be so limited, but rather will find utility with a broad range of oocytes.

While the illustrative embodiments of the invention have been described with particularity, it will be understood that various other modifications will be apparent to and can be readily made by those skilled in the art without departing from the spirit and scope of the invention. Accordingly, it is not intended that the scope of any claims ultimately obtained from applications dependent upon this provisional application be limited to the examples and descriptions set forth herein but rather that such claims be construed as encompassing all the features of patentable novelty which reside in the present invention, including all features which would be treated as equivalents thereof by those skilled in the art to which this invention pertains.

I claim:

1. A method of preparing a recipient oocyte from an oocyte harvested from a donor animal having a cytoplasmic membrane and chromosomal material within the membrane, the method comprising centrifuging the oocyte against a density gradient material at a centrifugal force that is at least great enough to force the chromosomal material to pass through the membrane but not so great as to destroy the membrane, thereby forming the recipient oocyte; and wherein the density gradient material has a density greater than the density of the harvested oocyte, and has a porosity sufficient to retain the harvested oocyte and yet permit the chromosomal material to pass through the membrane.

2. A method of preparing a recipient oocyte from a zona-free oocyte harvested from a donor animal having a cytoplasmic membrane and chromosomal material within the membrane, the method comprising centrifuging the oocytes against a density gradient material at a centrifugal force that is at least great enough to force the chromosomal material to pass through the membrane but not so great as to destroy the membrane, thereby forming the recipient oocyte wherein the density gradient material has a density greater than the density of the harvested oocyte, and has a porosity sufficient to retain the harvested oocyte and yet permit the chromosomal material to pass through the membrane.

3. A method of preparing a recipient oocyte from a zona-intact oocyte harvested from a donor animal having a cytoplasmic membrane and chromosomal material within the membrane, the method comprising removing the zona from the target oocyte; and centrifuging the oocyte against a density gradient material at a centrifugal force that is at least great enough to force the chromosomal material to pass through the membrane but not so great as to destroy the membrane, thereby forming the recipient oocyte wherein the density gradient material has a density greater than the density of the harvested oocyte, and has a porosity sufficient to retain the harvested oocyte and yet permit the chromosomal material to pass through the membrane.

* * * * *